United States Patent
Chang et al.

(10) Patent No.: US 6,535,625 B1
(45) Date of Patent: Mar. 18, 2003

(54) MAGNETO-ACOUSTIC IMAGING

(75) Inventors: David B. Chang, Tustin, CA (US);
James E. Drummond, Lincoln City, OR (US); Jane F. Emerson, Irvine, CA (US)

(73) Assignee: Magnetus LLC, Irvine, CA (US)

( * ) Notice: Subject to any disclaimer, the term of this patent is extended or adjusted under 35 U.S.C. 154(b) by 0 days.

(21) Appl. No.: 09/405,236

(22) Filed: Sep. 24, 1999

(51) Int. Cl.[7] .................................................. G06K 9/00
(52) U.S. Cl. ...................................... 382/128; 600/407
(58) Field of Search ............................... 328/128, 131, 328/132; 123/922; 250/455

(56) References Cited

U.S. PATENT DOCUMENTS

| | | | |
|---|---|---|---|
| 4,543,959 A | * 10/1985 | Sepponen | 324/309 |
| 5,402,786 A | * 4/1995 | Drummond | 324/318 |
| 5,438,999 A | * 8/1995 | Kikuchi et al. | 310/336 |
| 5,924,986 A | * 7/1999 | Chandler et al. | 600/407 |
| 6,174,284 B1 | * 1/2001 | Lillegard et al. | 600/443 |
| 6,306,095 B1 | * 10/2001 | Holley et al. | 600/458 |

OTHER PUBLICATIONS

Hall Effect Imaging by Han Wen et al. IEEE Transactions On Biomedical Engineering, vol. 45, No. 1, Jan. 1998, pp. 119–124.*

* cited by examiner

*Primary Examiner*—Jon Chang
*Assistant Examiner*—Charles Kim
(74) *Attorney, Agent, or Firm*—MacPherson Kwok Chen & Heid LLP

(57) ABSTRACT

An apparatus having a coil of wire, energized by a repetitively pulsed radio frequency (RF) power source to provide electromagnetic fields to a region within a body. A scanning, directional hydrophone acoustically connected to the body, samples ultrasonic radiation generated by the RF fields at the RF frequency or twice the RF frequency induced from conductive spots. Signals from the hydrophone are analyzed with regard to their time of arrival relative to the RF pulses and with respect to their direction of arrival. These collected data are recorded and displayed as images of the spots within the region.

19 Claims, 2 Drawing Sheets

MAGNETO-ACOUSTIC IMAGING

BACKGROUND OF THE INVENTION

1. Field of the Invention

The present invention relates primarily to medical diagnostic equipment generating RF fields and using directional ultrasonic detectors, it can also be applied to characterization of materials and components in non-medical fields.

While the present invention is described herein with reference to illustrative embodiments for particular applications, it would be understood that the invention is not limited thereto. Those having ordinary skill in the art and access to the teaching provided herein will recognize additional modifications, applications, and embodiments within the scope thereof and additional fields in which the present invention would be of significant utility.

2. Description of Related Art

Radio frequency (RF) electromagnetic (EM) fields are widely used for medical diagnostics in magnetic resonance imaging (MRI). In MRI, RF is used to excite coherent precession of nuclear magnetic moments in a strong static background magnetic field. These processing moments then provide imaging information through the RP fields that they generate. Imaging occurs through detection of the subsequent re-emission RF fields that depend on the local densities of moments, their relaxation times, and precession frequencies. Good spatial resolution is achievable (5 micrometers).

Ultrasound has been used to characterize the structure and quality of tissue in a volume imaged by MRI. (U.S. Pat. No. 4,543,959 issued 1985 to Seponen.) MRI is used to sense organ motion produced by transverse acoustic waves launched into the patient to characterize tissue properties. (R. Muthupillai, D. J. Lomas, P. J. Rossman, J. F. Greeleaf, A. Manduca, R. L. Ehman "Magnetic Resonance Elastography: Direct Visualization of Propagating Acoustic Strain Waves" Science 269 Sep. 29, 1995.)

Another approach to diagnostic imaging is supplied by Han Wen, Jatin Shah, & Robert S. Balaban "An Imaging Method Using the Lorentz Force of a Strong Magnetic Field—Hall Effect Imaging" Pros, Soc. Magn. Reson. Med." Vancouver, B. C., p.279, May 1997. This latter approach requires application of electrical voltages to electrodes on the patient in a very strong steady (DC) magnetic field with detection of resulting ultrasound or the launching of intense ultrasound in the DC magnetic field with detection of the resulting voltage on electrodes.

The apparatus in all these cases is expensive and bulky because of the large DC magnetic fields used. Because of the cryogenics needed to support the DC field currents, the machines are awkward for use in remote locations.

Microwave EM imaging without magnetic resonance has been considered for medical diagnostics ("Medical Application of Microwave Imaging", L. E. Larson & J. H. Jacobi Eds. IEEE Press, N.Y., 1985.) Excellent image contrast is produced because of the large variation of microwave refractive index among soft body tissues. However, these large variation deflect the paths of the microwaves traversing the body and thus distort the image produced. This effect also causes variable concentration of microwave power dosage in organs.

The injection of electrical currents and observation of resulting voltages at electrodes fixed to a patient have been studied as an imaging method ("Electrical Impedance Tomography" J. G. Webster Ed., Adam Hilger, Bristol & New York, 1990; "Evaluation of impedance technique for detecting breast carcinoma using a 2-D numerical model of the torso" Radai M. M., Abboud S., Rosenfeld M., Ann NY Acad Sci Apr. 20; 1999 873:360–9]. These methods are particularly significant in view of findings that breast cancer tumors have electrical conductivity four times that of surrounding normal tissue (D. C. Barber and B. H. Brown, "Clinical and Physiological Applications of Electrical Impedance Tomography" University College London Press, London, 1993; B. Blad and B. Baldetorp "Impedance spectra of tumor tissue in comparison with normal tissue; a possible clinical application for electrical impedance tomography," Physiological Measurement 17, A105 (1996); Holder D. S., et al. "Assessment and calibration of a low-frequency system for electrical impedance tomography (EIT), optimized for use in imaging brain function in ambulant human subjects." Ann N Y Acad Sci. Apr. 20, 1999; 873:512–9.) Imaging of tissue conductivity from such measurements involves inverting an elliptic differential equation which smooths out source details at distant observation points. This process is unstable in the sense that a small change in the observations produces large changes in the computed image. (Margaret Cheney "Inverse Boundary Value Problems" Am. Scientist 85 pp 448-55 (1997)).

To avoid the application of electrodes to the body, alternating magnetic fields have been used to produce images from currents in a phantom and a human thorax during respiration ("Magnetic impedance tomography" Ann N Y Acad Sci Apr. 20, 1999; 873:353–9, Tozer J. C., Ireland R. H., Barber D. C., Barker A. T.) A problem with magnetic detection at sub-microwave frequencies is its inherently low resolution, MRI avoids this problem because of the spatially-dependent resonant frequencies which define position.

SUMMARY OF INVENTION

The present invention consists of an apparatus and associated non-invasive method for imaging internal regions of interest without the confinement and expense of a strong DC magnetic field, without the geometric distortion inherent in microwave or magnetic imaging and without the use of voltage electrodes on the patient. The apparatus is comprised of a pulsed RF source driving current through one or more induction coils adjacent to a bed supporting the patient and a scanning directional ultrasonic microphone or hydrophone. The detected output of the hydrophone and values of its look angles are fed to a video memory used for image construction off line or on line. The method consists of applying a pulse of RF current to the coils, detecting and recording the resulting ultrasonic signals which appear at twice the applied RF frequency; images of volumes within the patient are constructed by use of an algorithm applied to the recorded data. An alternative version uses a small DC magnetic field in addition to the RF EM field. Signals are then detected at the applied RF frequency as well.

DESCRIPTION OF INVENTION

Figure 1:
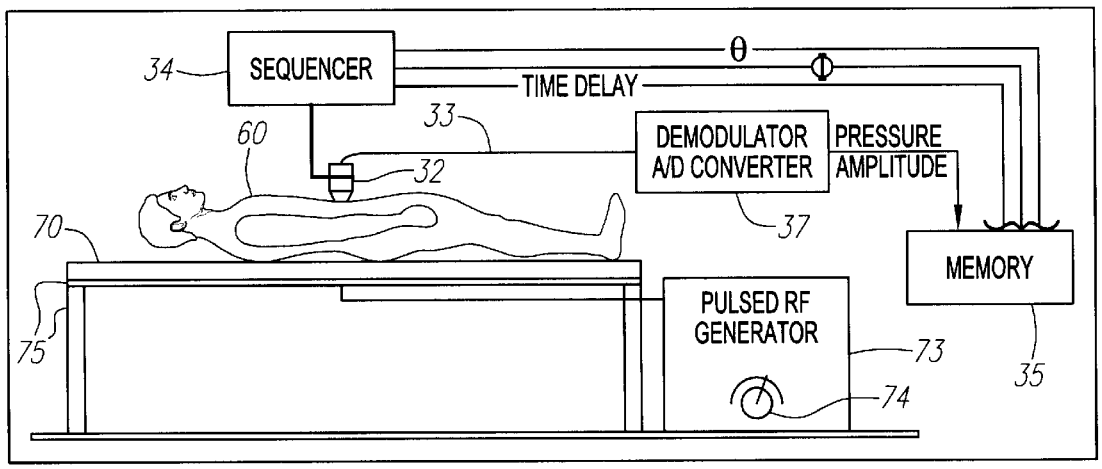
FIG. 1 is a side view of a patient lying on a bed above a coil driven by a pulsed RF source of current, showing a directional ultrasonic sensor supplying signals to an RF detector and amplifier that distribute data sequentially to an electronic random access memory.
Figure 3:
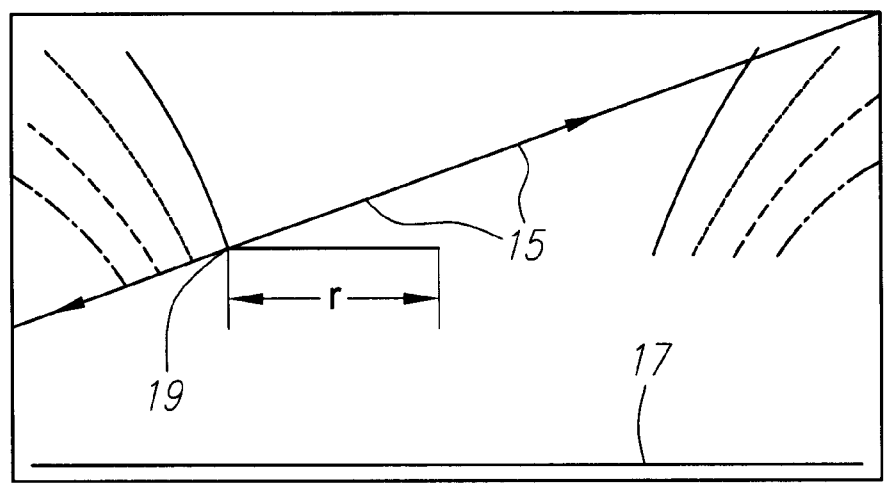
FIG. 3 is a representation of the RF magnetic field within a volume of the patient along with an indication of the induced electric fields, currents, and ultrasonic radiation.

FIG. 1 shows current from a pulsed RF generator 73, driven through a coil 21, underneath a patient 60, lying on a water bed mattress 70, supported by table 75. FIG. 3 plots some fringing RF magnetic field lines (radius vs height) above the coil 17, shown as a dark horizontal line at the bottom of the figure.

We consider the generation of ultrasound from nonresonant RF EM fields. The mechanism consists in the generation of Ohmic currents from the electric field portion of the RF EM field, the currents in turn interacting with the magnetic field (either the magnetic portion of the RF field and/or a background static field) to generate ultrasound. In the latter case, sizable ultrasound imaging signals will be generated at both the RF frequency and at twice the RF frequency, whereas in the absence of a static magnetic field, ultrasound imaging signals will be generated at twice the RF frequency only.

The method provides different information about the body than conventional ultrasound or MRI, in that here the primary feature imaged is electrical conductivity rather than variations in acoustic parameters or nuclear moment relaxation times and precession frequencies.

A detailed description of the invention's operation uses the following set of six equations: the generalized Ohm's law, momentum equation, continuity equation, constitutive equation relating pressure to density, and Lenz's law for the magnitude of the electric field around a small circular region within a body. In their lowest approximations:

| | | |
|---|---|---|
| Generalized Ohm's law: | $j = \sigma(E + V \times B)$ | (1) |
| Momentum equation: | $\rho \, dV/dt = -\nabla p + j \times B$ | (2) |
| Continuity equation: | $\partial \rho/\partial t + \nabla (\rho V) = 0$ | (3) |
| Pressure equation: | $p = \rho V_s^2$ | (4) |
| Lenz's law: | $E = d[rB_1/2]/dt$ | (5) |

Here, j denotes the current density, $\sigma$ is the conductivity, E and B are the electric and magnetic fields, p is the mass density, p is the acoustic pressure, Vs is the speed of sound in body material, and V is the gross mass velocity. For generality, B consists of a Static portion $B_0$ and an RF portion $B_1$ oscillating with an angular frequency $\omega$, although later we shall consider what happens when the static portion is absent. System International (SI) units are used.

These equations apply when the frequency is less than the plasma and collision frequencies and the Debye Shielding length is less than any spatial variation of interest, for under those circumstances charge neutrality is satisfied. These conditions are well satisfied for the imaging applications of interest, since in body electrolytes, typical plasma and collision frequencies are of the order of $10^{12}$/s and typical shielding distances are less than a micrometer.

The physics of generating an ultrasound signal by applying an oscillating EM RF field is as follows: The electric field portion of the RF EM field induces an Ohmic current via eq. (1). The ultrasound motion and pressure that this current causes are determined via eqs. (2)–(4), and are quite small. In fact, the velocity is so small that the V×B term in eq. (1) is much smaller than the E term and can be ignored. Nevertheless, for reasonable parameters, an easily measurable ultrasound pressure wave results.

Approximating the RF magnetic field $B_1$ of angular frequency $\omega$ as a locally uniform field in the z direction at a distance, $r_0$ out from the axis of the cylindrical coil, we have from Lenz's law for the magnitude of the RF electric field:

$$E = r_0 B_1/2 \qquad (5A)$$

Upon ignoring the magnetic term in the generalized Ohm's law of eq. (1)—which is verified later as a legitimate law of eq. (1)—which is verified later as a legitimate thing to do, this electric field induces an electric current density of magnitude $$j = \sigma E \qquad (6)$$

The invented method provides information on the spatial variation of tissue electrical conductivity, and does this by measuring the ultrasound pressure radiated by the interaction of induced RF Ohmic currents with either a static or the inducing RF magnetic field. In the following, the general imaging equation will be discussed along with the implications of tissue electrical conductivity measurement.

For the general case, on combining eqs (2)–(4), and (6):

$$\nabla^2 P - V_s^{-2} \partial^2 P/\partial^2 t^2 = \nabla \cdot [\sigma E \times B] \qquad (13)$$

It is significant that this is a hyperbolic partial differential equation rather than the elliptic equation which is involved in Electrical Impedance Tomography. This avoids smearing source data, redocing instability and improving image fidelity. [Margaret Cheney, op cit] F-or solution, one may Replace the second time derivative by $-\omega^2$ and defining $$k^2 \omega^2 V_s^{-2} \qquad (14)$$

Integrating by parts over the volume examined by the ultrasound sensor gives $$P_\omega \approx -i(\exp(ik_\omega R)/R) \int d^3r \, \exp(ik_\omega \cdot r) \sigma(r)(E \times B)_\omega \cdot k_\omega \qquad (15)$$

Where we have used the condition that $|E \times B|$ varies much more gradually than $\sigma(r)$ and that it goes to zero at the boundaries of the observation region. This may be attained by using small enough induction coils close to the region of interest. The right hand side of this equation is the source term, a Fourier transform with a weighting factor given by the component of E×B along the observation direction, k. EQ.(15) shows that the ultrasound generated by the Ohmic currents gives information primarily on the spatial variation (Fourier components) of the conductivity. These variations reflect changes in ionic concentrations, viscosities, and the volume fraction available for current flow. The latter two are related, as effective viscosities will depend on the presence of obstructions to fluid flow.

Imaging conductivity variations should provide useful complementary information to that given by conventional ultrasound and MRI techniques, especially to visualize heart and lungs. [5, Kimura, T, Morimoto, T. Uyama, Y. Monden, Y. Kinouchi, T. Iritani "Application of electrical impedance analysis for diagnosis of a pulmonary mass," Chest 105(6), 1679 (1994)]

Conductivities vary considerably from tissue to tissue. [D. C. Barber and B. H. Brown, loc. elk. And Sci. Instrum 17 723–33 (1984)] give the following conductivities for frequencies in the 20–100 KHz range. These values increase −30 from 100 kHz to 10 MHz.

TABLE 1

Organ Tissue Conductivity

| Tissue | Conductivity in siemens/m |
|---|---|
| Cerebrospinal fluid | 1.5 |
| Plasma | 1.5 |
| Blood | 0.67 |
| Liver | 0.29 |
| Human arm | 0.42 (longitudinal) |
| | 0.15 (transverse) |
| Skeletal muscle | 0.67–0.8 (longitudinal) |
| | 0.043–0.056 (transverse) |
| | 0.19 (average) |
| Cardiac muscle | 0.17–0.625 (longitudinal) |
| | 0.019–0.24 (transverse) |
| | 0.13 (average) |
| Neural tissue | 0.17 |
| -gray matter | 0.35 |
| -white matter | 0.15 |
| Lung | 0.04–0.138 |
| Fat | .04 |
| Bone | $6\, 10^{-3}$ |

EQ.(15) shows that by scaling the frequency of $B_1$ with the inverse of the tumor thickness, the peak ultrasonic pressure also increases as the thickness decreases. Thus the present invention allows early detection of very thin tumors and by sweeping the frequency, tumor thickness can be inferred from nodes in the ultrasonic signal magnitude.

In the foregoing, we ignored the V×B term of EQ-(1) compared to the E term. From eq. (2), it can be seen on using eq (5) for E that $$V = 0[srB_1B_0/r] \qquad (16)$$

This then gives $$VB_0/(E) = O[sBo^2/(rw)] \qquad (17)$$

Substitution of the practical numbers into EQ. (17) shows this ratio to be very small, justifying the approximation used.

J. W. Woodbury, S. H. White, M. C. Mackey, W. L. Hardy, D. B. Chang, "Bioelectrochemistry," Chapter 11 in Physical Chemistry, An Advanced Treatise, ed. Henry Eyring, New York: Academic Press (1970), set a lower limit on the RF frequency that can be used for generating ultrasound from induced Ohmic currents. The desired condition is that the impedance associated with the membrane capacitances should be less than the impedance due to electrolyte resistivity. Then the induced voltages will be primarily available to drive the Ohmic currents. This condition may be written roughly as $$|Z_C/Z_\rho| = (\omega C_1 \rho_e d)^{-1} << 1 \qquad (18)$$

where $Z_C$ is the impedance of the membrane capacitance, $Z_\rho$ is the impedance of the electrolyte, $\omega$ is the angular frequency of the RF, $C_1$, is the membrane capacitance per unit area, $\rho_e$ is the resistivity of the electrolyte, and d is a typical dimension of an Ohmic path—which we shall take to be a typical dimension of a cell. For practical numbers, this sets the lower limit on angular frequency at one MHz. With acoustic velocities, $V_S$, of $1.5 \times 10^5$ cm/sec, this says that the corresponding acoustic wavelengths will be less than 1.5 mm. [A 1 mm wavelength corresponds to a frequency of 1.5 MHz.] Since we are interested in features of this size or smaller, the frequency limitation is no problem.

The spatial resolution obtainable by this method should be at least comparable to that obtainable with conventional ultrasound techniques. The same scattering losses which limit resolution in conventional ultrasound will also be present here. There may be some improvement due to the fact that the sound waves only need to propagate from the body source to the detector, rather than make the two-way circuit of the conventional transducer approach. To the extent that conductivity variations are much larger than acoustic impedance variations—e.g. the difference of electrical conductivity by a factor of 4 between cancerous and noncancerous breast tissue versus 10–20% variation in acoustic impedance, some of the extra large contrast can be used to enhance tumor edge location.

The coil radius in FIG. 3 was taken as 0.48 m. At the base of the inner curve on the left is a 1 cm diameter area, 19, shown to scale which could, for instance, represent a one centimeter cancerous tumor which has conductivity of 0.16 siemens/m, substantially larger than that of the surrounding tissue. The current induced by the oscillating flux is acted upon by the oscillating magnetic field. This produces a force density oscillating at twice the frequency of the magnetic field and acting back and forth along the line, 15, indicated by arrows. This is the axis along which ultrasonic waves will be projected, forward and backward, in two cones.

The force density integrated along the one cm length of the tumor will produce acoustic pressure at the source, 19. The intensity (proportional to wave pressure squared) of these waves will be attenuated in traveling through adjacent tissue; fat for example, by about 3 dB/cm. Thus for 10 cm travel from source to sensor, the acoustic pressure will drop by 30 db. Using a 100 to 1 concentrating reflector incorporated within housing, 32, of FIG. 1 will increase intensity by 20 db, the acoustic pressure by a factor or ten.

Housing 32 contains or is driven by a sequencer 34 and, for instance, a stepping motor driven acoustic mirror so that the sensor receives ultrasonic signals from a sequence of angles e.g. measured with respect to local vertical and the direction of the Earth's DC magnetic field. The sequencer detects a remnant of RF induction from the pulsed RF generator via coil 21; it cycles through a series of delays, scanning range, and activates angular pointing of the reflector shown in FIG. 4, which surrounds the ultrasonic sensor within housing 32. Amplitude detected during a gated short interval following the delay together with the imposed (digital) delay, and the digital azimuthal and polar angles at that time are fed to memory. 35 as shown in FIG. 1.

Figure 2:
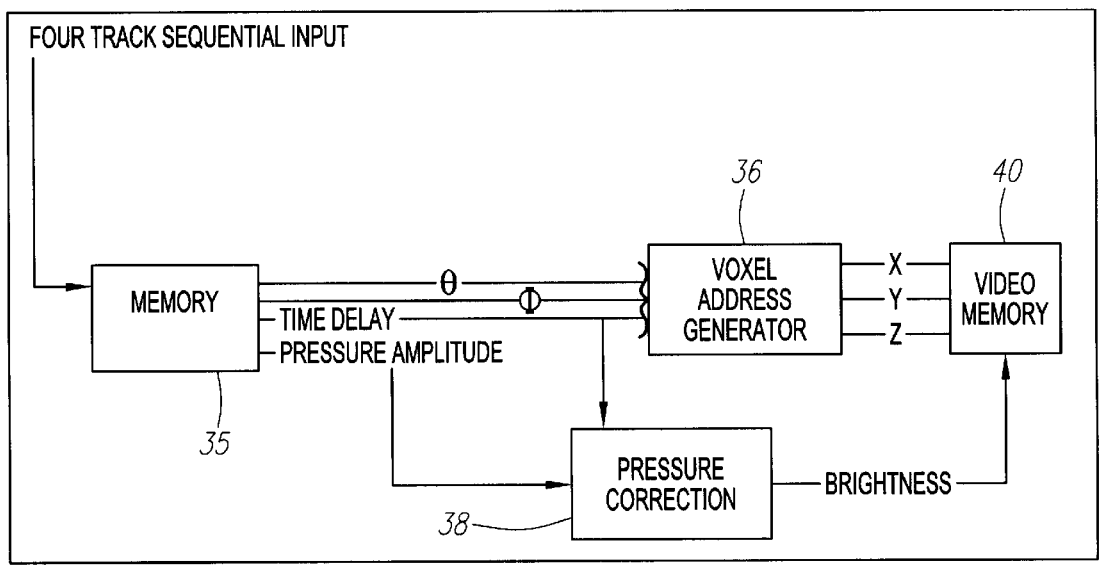
FIG. 2 is a block diagram, showing image construction from the memory data.
Figure 4:
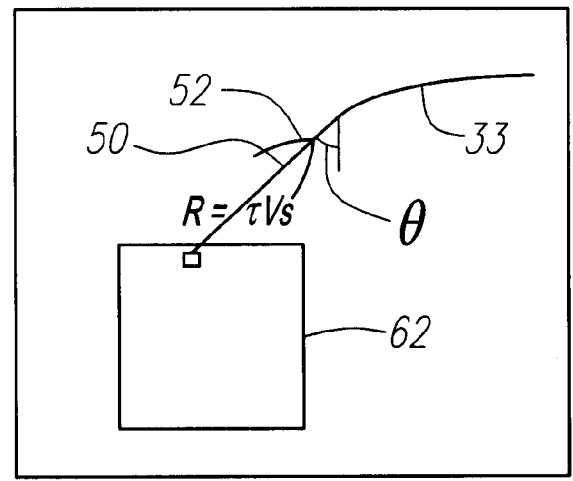
FIG. 4 is a block diagram showing the subsystem for correcting raw acoustic pressure data.

FIG. 2 is a block diagram of the image construction process. The four track output of memory 35 is separated into two parts, the three elements that determine the location of the object pointed at and the pressure of the ultrasonic wave from that location. In order to convert the observed pressure signal to source pressure signal, it is necessary to use a time gain compensating (TGC) amplifier as used in standard ultrasound imaging, indicated by Pressure Correction unit 38. The unit simply multiplies the pressure amplitude by $\exp(\alpha \tau V_S)$ where $\alpha$ is the pressure attenuation coefficient in nepers/m, $\tau$ is the delay time in seconds and $V_S$ is the speed of sound in m/s. In addition, the pressure output of memory 35 is combined with angle outputs to locate the signal source in a 3D Coordinate system. FIG. 4 provides an illustration of the geometry applicable to that task. Parabaloidal mirror 52 focuses the ultrasound it receives from the volume of interest, 62, onto the sensitive area at the tip of PZT sensor 50 which sends its analog signal via cable 33 to Demodulator and A/D converter 37. The angle between the negative vertical axis and the axis of the reflector is Θ.

Angles around the vertical axis are designated by $\Phi$. The coordinates of the voxel ultrasound source are given by $$X=R\sin(\Theta)\cos(\Phi)\ Y=R\sin(\Theta)\sin(\Phi)\ Z=R\cos(\Theta)$$

where $R=\tau V_S$ with $\tau$ the delay time in ms and $V_S$ the speed of sound in soft tissue ~150 cm/ms. FIG. 2 shows a time sequence of X, Y and Z inputs to video memory 40 from a voxel address generator 36. This assigns the brightness at each instant to the address generated at that instant. Video memory 40 can be any standard type of video memory, such as analog rasters or switched digital memory arrays. Other scanning procedures could be used. This one is convenient because a rapid oscillating scan is easy in the $\Phi$ direction and a slower oscillating scan is easy in the $\Theta$ direction but it does make interpolation between step locations necessary for uniformly dense voxel locations.

The PZT crystal together with its loading capacitors is preferably set to resonate with the ultrasound frequency produced by the oscillating magnetic field.

The $\Theta$, $\Phi$ resolution of acoustic imaging will depend strongly on the acoustic optics of the ultrasound detection system. Equation (15) is a solution of a standard wave propagation equation with a source term, and so the same general considerations that define images in regular optical systems with lenses and mirrors can be applied here.

As an example, a simple spherical wave reflector may be used instead of the preferred paraboloidal mirror to focus the ultrasound from the source region onto a piezoelectric detector. Denoting the radius of the mirror by R, the distance from the mirror to a source point by s and the distance from the mirror to the image point by s', then we have from optics $$1/s-1/s'=-2/R \quad (19)$$

The corresponding lateral magnification m is $$m=s'/s \quad (20)$$

If s=15 cm, and R=15 cm, then s'=3 cm, and the transverse magnification is ⅓. For a real image closer to the mirror than the source point, there will be demagnification. Using a simple convex acoustical lens both of whose surfaces have radius of curvature R and for which the acoustical index of refraction is n, then with the source point to the left of the lens at a distance s from the lens, and an image point to the right of the lens at a distance s', we have the relation $$1/s+1/s'=1/f \quad (21)$$

where the focal point of the lens is given by $$1/f=(n-1)(2/R) \quad (22)$$

(assuming that the acoustic index of refraction of the surrounding medium is unity), and the lateral magnification m in this case is $$m=-s'/s \quad (23)$$

For s=15 cm, R=4 cm, and n=1.2, then s'=30 cm, and a=~2.

This method is to locate a piezoelectric sensor on the axis of a mirror or lens, and rotate the mirror or lens to scan the source region, in this technique, the distance to the source is varied by changing the distance of the piezoelectric sensor from the mirror.

Ultimately, the basic optics resolution limit is given by the diffraction angular limitation of $\lambda/D$, where $\lambda$ is the acoustic wavelength and D is the diameter of a typical acousto-optical element.

An array of sensors is used to increase D and improve the resolution. If the distance from the source to collection system is L, then the transverse resolution is roughly $(\lambda/D)L$. Thus, the smallest practical transverse dimension resolvable is of the order of a wavelength. A 1 mm resolvable dimension corresponds to an ultrasound frequency of 1.5 MHz.

In addition to the acousto-optics limitations, the resolution obtainable with ultrasound imaging is also limited by the attenuation and/or scattering of the ultrasound as it propagates through the medium between the source and detector.

Sample attenuation coefficients for I MHz ultrasound in various tissues are listed below [Matthew Hussey, *Basic Physics and Technology of Medical Diagnostic Ultrasound*. New York: Elsevier, 27 (1984)], along with the corresponding inverse absorption lengths for the ultrasound pressure (as opposed to ultrasound intensity).

TABLE 2

Experimental Data for 1 MHz Sound in body tissues.

| Tissue | $\alpha$ (nepers/cm) | $V_s$ (m/s) | Char. Impedance ($10^6$ kg m$^{-2}$s$^{-1}$) |
|---|---|---|---|
| Water | $2.9 \times 10^{-4}$ | 1480 | 1.48 |
| Fat | 0.04–0.09 | 1410–1470 | 1.34–1.39 |
| Brain | 0.07 | | |
| Liver | 0.08–0.11 | 1550 | 1.66 |
| Kidney | 0.10–0.13 | 1560 | 1.63 |
| Muscle with grain cross grain | 0.17–0.24 0.21–0.40 | 1590 | 1.71 |
| Heart | 0.13 | | |
| Spleen | 0.060 | 1550 | 1.65 |
| Eye Vitreous | 0.012 | 1520 | 1.52 |
| Amniotic Fluid | 0.00081 | 1510 | 1.5 |
| Air | 1.4 | 380 | 0.004 |
| Bone | 1.4 | 4080 | 7.8 |

[Frederick W. Kremkau Compiled from, Diagnostic Ultrasound: Principles, Instruments and Exercises. Philadelphia: W.S. Saunders Co, 34 (1989); James F. Havlice, Jon C. Tanzer "Medical Ultrasonic Imaging; An Overview of Principles and instrumentation" in Modern Acoustical Imaging Hua Lee, & Jon wade, Eds.]

The attenuation, $\alpha$, of acoustic pressure increases with frequency f in the range of 0.1–10 MHZ by a factor of about $f^{1/2}$, intensity by the factor f. [James f. Havlice, Jon C. Tanzer, loc. Cit. and Eriko Tohno, David O. Cosgrove, John P. Sloane, Efthiklis Vagios Ultrasound Diagnostics of Breast Diseases Churchill Livingstone, Nf (1994) and.]

The magnets or coils to provide a large static magnetic field are expensive, so there is significant cost advantage to techniques that do not require a large static background magnetic field. The invented technique can be used either with a static background field or without one.

The equations show that it is possible to use only the $j \times B_1$ term as the source of the ultrasound (deleting the $j \times B_0$ term associated with a static background field). This entails some combination of (1) dealing with lower ultrasound pressures and of (2) increasing the ratio of average RF EM field strength to RF frequency.

Since the amplitude of the $\omega$ frequency ultrasound is proportional to $B_0 B_1$ and the 2 $\omega$ frequency ultrasound is proportional to $B_1^2$, the same level of ultrasound as generated in the static field could be gotten without the static field by increasing the RF field to 0.001 tesla. However, at that level, the allowable FSA-permitted steady-state power input of 5W per kg would be exceeded. The power would be too large so the RF field would have to be reduced or the duty cycle kept low. The latter is easily accommodated with a large safety margin.

The ohmic heating per unit body mass per unit time due to RF field would be $W=(½) \sigma E^2 DC/(10^3 kg/m^3)$ where DC, is duty cycle expressed as a fraction. The ratio of generated acoustic pressure to W is increased by using lower frequencies and duty cycles. Lower duty cycle means longer time required for imaging. This can be compensated by using an array detector so that each pulse produces data for many image pixels, rather then just one as in the preceding illustrative figures and discussion. For example, the single PZT sensor 50 of FIG. 4 can be replaced by a 16×16 array of PZT sensors. This will, of course, require that the number of $\Theta$, $\Phi$ and pressure data channels indicated in FIG. 2 be increased by a factor of 256 though a single time delay signal could serve for all of these. There is thus a small reduction of required memory channels.

A disadvantage of using the 2 $\omega$ signal is that its attenuation is 40% greater than the $\omega$ signal. PZT sensors can detect $10^{-6}$ Pa and fiber optic sensors are even more sensitive.

Contrast provided by the invention should be large relative to that obtainable with ultrasound imaging alone because of the large ratio of conductivities in the body versus the small acoustic reflection coefficients. The latter may be seen from the formula for reflection coefficients of acoustic waves normally incident on soft tissue:

$$R=(Z_2-Z_1)/(Z_2-Z_1)$$

and the values of soft tissue impedances, Z, from table 1. The largest value of R for reflection of a wave from water to a soft tissue is from water to muscle: 7.2%. Compare this with the 400% conductivity increase of cancer over surrounding breast tissue.

Along with the small reflection there is small refraction of ultrasound in body tissues. This may also be seen from Table 2. The largest variation of refractive index differs from that of water by only 13%.

The above description deals with one embodiment of an apparatus according to the invention. Other possible embodiments include an ultrasonic sensor assembly imbedded in an oil or water bed acoustically connected to a patient's body.

In practice, image data from target regions of interest can be referenced to other within-organ regions, contralateral regions, or be compared with stored image data obtained from apparently healthy, diseased, or anomalous tissues.

We claim:

1. Imaging apparatus for collecting information on internal structure and properties of a target region within an object selected to be examined, said apparatus comprising:
   means for supplying a sequence of pulsed nonresonant RF electromagnetic fields which induces currents within conductive tissue volumes of said target region selected to be examined such that said currents can interact with a magnetic field component of said nonresonant RF electro-magnetic field and with a steady magnetic field to produce ultrasound signals at an applied radio frequency and at twice the applied radio frequency;
   means for detecting and means for recording said ultrasound signals;
   means for processing the information obtained by said means for detecting said ultrasound signals; and
   means for visually displaying the target volume and the information.

2. Imaging apparatus as claimed in claim 1, wherein said means for detecting said ultrasound signals comprises angled sensors and time delay gating from initiating electromagnetic pulses for selecting and registering the time and the direction from which the ultrasound arrives at said means for detecting ultrasound signals.

3. Imaging apparatus as claimed in claim 1, wherein said means for supplying pulsed nonresonant RF electromagnetic fields comprises a coil assembly operable to transmit said pulses.

4. Imaging apparatus as claimed in claim 1, wherein said means for detecting said ultrasound signal comprises a concave reflector surrounding one or more pressure sensitive elements.

5. Imaging apparatus as claimed in claim 1, wherein said means for detecting said ultrasound signals comprises a plurality of pressure sensitive elements.

6. Imaging apparatus as claimed in claim 1, wherein said means for detecting said ultrasound signals comprises a converging acoustic lens focused on one or more pressure sensitive elements.

7. A method for detecting and diagnosing anomalies and pathological changes in tissue structures of a biological object to be examined by simultaneously collecting information on tissue structure and properties of the tissues, said method comprising:
   transmitting a sequence of radio frequency electromagnetic pulses into a given target area of said biological object selected for examination to produce a nonresonant RF EM field to induce currents in tissue within said target area selected for examination using a charge current density created by an electric field component of said nonresonant RF electro-magnetic field such that said current can interact with a magnetic field component of said nonresonant RF electromagnetic field and a steady magnetic field to produce ultrasonic emissions at both an applied radio frequency and at twice the applied radio frequency;
   detecting and recording said ultrasonic emissions from diseased and healthy portions of said biological object distinguished by their distinctive electrical conductivity difference;
   detecting said emissions with directional ultrasonic detectors; and
   recording said detections of said emissions together with the corresponding angles and times of arrival of said detections of said emissions.

8. A method as claimed in claim 7, further comprising visualizing the information collected.

9. A method as claimed in claim 7 further comprising:
   storing information from a number of said recordings; and
   comparing the information received from the target tissues under examination with the stored information.

10. A method as claimed in claim 7 wherein said RF signal is swept in frequency, producing ultrasound intensity from a thin highly conductive region, wherein said intensity passes through a series of nodes; said nodes used to determine a thickness of the highly conductive region.

11. A method as claimed in claim 10 wherein said thickness of the highly conductive region is determined from a plurality of directions from said directional ultrasonic detectors, and is used to form an image of highly conductive regions.

12. Imaging apparatus as claimed in claim 1, wherein said means for detecting detects ultrasound at the applied frequency and at twice the applied frequency.

13. A method as claimed in claim 8 further comprising:
   storing information from a number of said recordings; and
   comparing the information received from the target tissues under examination with the stored information.

14. Imaging apparatus comprising:

a pulsed RF generator coupled to a coil assembly operable to transmit RF pulses for generating a pulsed nonresonant RF EM field, an electric field component of said nonresonant RF EM field and with steady magnetic field generating a current within a target region of tissue being examined, said current interacting with a magnetic field component of said nonresonant RF EM field to produce ultrasound imaging signals at twice said radio frequency and at said radio frequency;

means for detecting and recording said ultrasound imaging signals;

means for processing data detected by said means for detecting said ultrasound imaging signals; and means for visually displaying said processed data.

15. The imaging apparatus of claim 14, wherein said means for detecting said ultrasound imaging signals comprises at least one angled sensor and a time delay gating from initiating magnetic pulses for selecting and registering the time and the direction from which the ultrasound imaging signals arrive at said means for detecting said ultrasound imaging signals.

16. The imaging apparatus of claim 14, wherein said means for detecting ultrasound imaging signals comprises a concave reflector surrounding one or more pressure sensitive elements.

17. The imaging apparatus of claim 14, wherein said means for detecting ultrasound imaging signals comprises an array of pressure sensitive elements.

18. The imaging apparatus of claim 14, wherein said means for detecting ultrasound imaging signals comprises a converging acoustic lens focused on one or more pressure sensitive elements.

19. A method for detecting and diagnosing anomalies and pathological changes in tissue structures comprising:

generating a pulsed nonresonant RF EM field using a pulsed RF generator coupled to a coil assembly operable to transmit RF pulses, an electric field component of said nonresonant RF EM field generating a current within a target region of tissue being examined, said current interacting with a magnetic field component of said nonresonant RF EM field and with a steady magnetic field to produce ultrasound imaging signals at twice said radio frequency and at said radio frequency;

detecting and recording said ultrasound imaging signals;

processing data detected by said step of detecting said ultrasound imaging signals; and visually displaying said processed data.

* * * * *